United States Patent [19]

Runge et al.

[11] 4,058,857
[45] Nov. 22, 1977

[54] CARDIAC REPLACEMENT PUMPING DEVICES

[76] Inventors: Thomas M. Runge, 2501 Galewood Place, Austin, Tex. 78703; John E. Burkhalter, 551 E. University Drive, Auburn, Ala. 36830; Spiros George Pallas, 130 Tenth Ave., Shalimar, Fla. 32579

[21] Appl. No.: 657,702

[22] Filed: Feb. 12, 1976

[51] Int. Cl.² .................... A61F 1/24; A61M 1/03
[52] U.S. Cl. ........................... 3/1.7; 417/412; 417/482
[58] Field of Search ............... 3/1.7, 1.4, 1; 128/1 D; 417/410, 412, 413, 482

[56] References Cited

U.S. PATENT DOCUMENTS

| 3,046,903 | 7/1962 | Jones | 3/1.7 X |
| 3,379,191 | 4/1968 | Harvey | 3/1.7 |
| 3,771,173 | 11/1973 | Lamb | 3/1.7 |
| 3,914,802 | 10/1975 | Reick | 3/1.4 |

FOREIGN PATENT DOCUMENTS

| 1,195,011 | 5/1959 | France | 3/1.7 |
| 2,052,876 | 5/1972 | Germany | 3/1.7 |

OTHER PUBLICATIONS

"A Prosthetic Heart with Hemispherical Ventricles Design for Low Hemolytic Action", by C. Kwan-Gett et al., Transactions American Society for Artificial Internal Organs, vol. XVI, 1970, pp. 409-415.

Primary Examiner—Ronald L. Frinks
Attorney, Agent, or Firm—B. P. Fishburne, Jr.

[57] ABSTRACT

A pumping device whose functioning resembles the action of the natural four chambered heart is constructed as a total cardiac replacement unit. An internal electrical drive motor adapted to be powered by radio frequency induction across intact skin drives an eccentric rotary element which in turn causes oscillation of pivoted vanes whose movements cyclically compress a pair of blood compatible sacs which simulate the left ventricle and right ventricle of the natural heart by pumping blood through the aorta and pulmonary artery, respectively. As in the natural heart, stroke volume of each ventricle is independent of the other and is a function of right atrial and left atrial pressure and volume. Additional embodiments of the invention feature modified driving means for the pumping vanes.

8 Claims, 10 Drawing Figures

1

CARDIAC REPLACEMENT PUMPING DEVICES

BACKGROUND OF THE INVENTION

Recent advances in heart surgery and cardiology have led to human heart transplantation and to the realization that the eventual solution to the problem of dealing with a failing heart may lie in the use of a man-made replacement device or pump.

At the present time, machines are being used in hospitals to bypass the natural heart and take over its function while surgery is being performed on the heart. Such machines are not constructed for use as cardiac replacement devices inside of the body, and up to the present time, no such means has been available, although research and development toward this end is underway.

The objective of this invention is, therefore, to provide a total cardiac replacement device or pumping unit which hopefully will advance the state of the art somewhat closer to the time when a man-made device can be successfully implanted in the body as a practical and permanent replacement for the natural heart which has failed. For such an event to become a reality, a large number of problems must be dealt with including the development of a small practical long-lasting power supply, creation of a sufficiently compact, durable and efficient pumping mechanism, and discovery of materials which are tissue-compatible, and the use of which device will maintain hemolysis within acceptable limits. Substantial progress is being made toward the solution of some of the above problems in the medical and engineering communities.

It is believed that the present invention is a significant advance in the art. More particularly, the invention embodies a pumping unit forming a total cardiac replacement device whose operation resembles the operation of the natural heart by providing a pulsatile flow of blood, a filling rate of ventricular sacs which is a function of right and left atrial pressure and volume, and an independent stroke volume for each ventricle sac depending on filling pressure within the sacs. In the device according to the several embodiments thereof, blood is contained within tissue compatible components and does not contact metallic parts.

Other features and advantages of the invention will become apparent during the course of the following detailed description.

DETAILED DESCRIPTION

Figure 1:
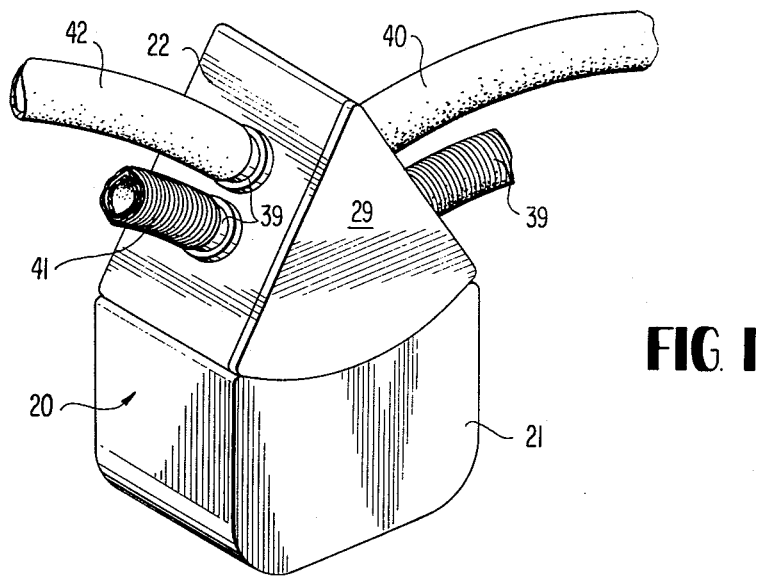
FIG. 1 is a perspective view of a cardiac replacement device embodying the invention according to one embodiment thereof.

Referring to the drawings in detail wherein like numerals designate like parts, and referring initially to FIGS. 1 through 4, a total cardiac replacement device or pumping unit is shown comprising a housing 20 having a lower electric motor compartment 21 and an upper pumping chamber or compartment 22 which is tapered and has the wedge-like form shown in the drawings. A small electric motor 23, such as a 1/100th horsepower motor, is adapted to be powered through radio frequency induction across the intact skin of the recipient. Such motors and induction coil means, not shown, are known in the art. The motor 23 has its armature or output shaft 24 projecting centrally into the lower relatively wide end of pumping chamber 22, the pumping and motor chambers being separated by an arcuate wall 25.

Figure 2:
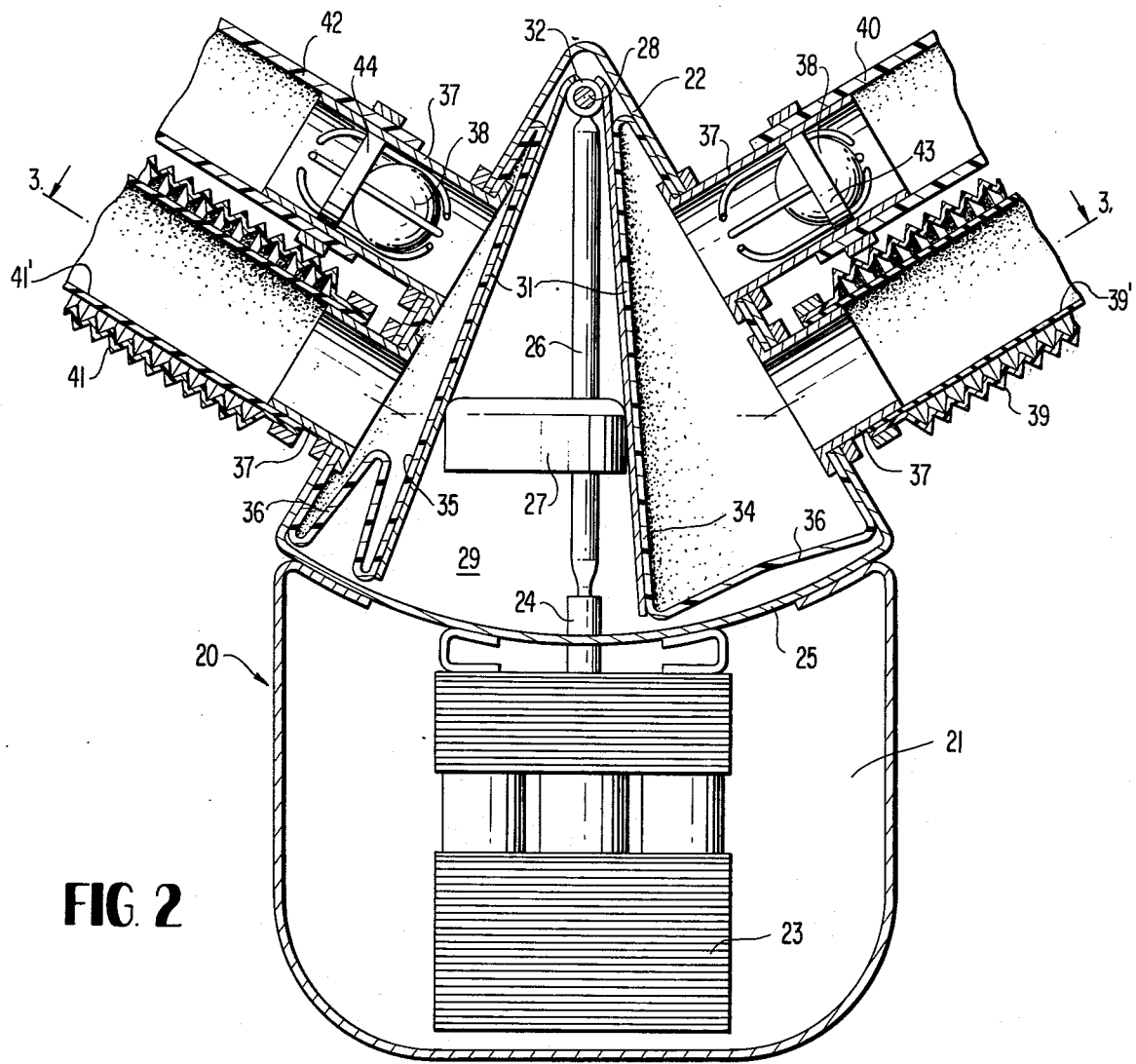
FIG. 2 is an enlarged central vertical section through the device.

Within the tapered pumping chamber 22 centrally and extending lengthwise thereof, FIG. 2, is a rotary shaft 26 whose lower end is coupled to the armature shaft 24 of the motor so as to be directly driven thereby. The rotary shaft 26 carries an eccentrically mounted circular cam 27 intermediate its ends and turning therewith.

Near the upper narrow end or apex of the pumping chamber 22, a support shaft 28 has its opposite ends supported on the side walls 29 of pumping chamber 22 and this shaft forms the pivotal support for a pair of pumping vanes 31 whose upper ends are welded or otherwise rigidly secured to knuckles 32 which are rotatably mounted on the support shaft 28. The knuckles of the two opposing flat vanes 31 interfit on the shaft 28 similarly to the construction of an ordinary door hinge. The mounting arrangement allows the vanes 31 to swing or oscillate independently on the axis of shaft 28 and sweep across the pumping chamber 22 between the divergent side walls thereof during the operation of the device. The stationary shaft 28 also forms the bearing means for the upper end of rotary shaft 26, such shaft having an upper tapered bearing element 33 received in a suitable seating recess of the shaft 28. The eccentric cam 27 and its drive shaft 26 is disposed between the vanes 31, whereby rotation of the cam will cause cyclic independent oscillation of the vanes while keeping their lower ends spaced apart in a V-shaped configuration, FIG. 2.

Between the side walls of pumping chamber 22 and the vanes 31 is disposed a pair of left and right ventricle sacs 34 and 35 of tapering configuration and preferably having pleated end walls 36. These two sacs simulate the left and right ventricles of a natural heart, and are formed of blood compatible material such as Silastic reinforced with Dacron, or equivalent material. Each ventricle sac is anchored to a side wall of the chamber 22 by a non-metallic pair of tubular fittings 37 which form the outlet and inlet for blood flowing from and returning to the ventricle sac 34 or 35. The fittings 37 form the mounting sites for plastic caged ball check valves 38 of a known type and these valves like the fittings 37 are formed of blood compatible material. A feature of the invention is that nowhere in the device does blood come into contact with metallic parts.

As illustrated, one check valve 38 for the left ventricle sac 34 is outwardly opening so that blood can be pumped from the sac 34 into the aorta 39 when the sac 34 is compressed. This same valve is inwardly closing to block any return flow of blood from the aorta into the sac 34. It corresponds to one of the two semilunar valves of the natural heart. The second valve 38 for the left ventricle sac 34 is the blood return or inflow check valve corresponding to the mitral valve of the natural heart and allowing blood to enter the left ventricle from the left atrium 40, which in turn receives blood from the pulmonary vein. It may be noted that in the device of the invention the right and left simulated atria are external to the pumping chamber 22 rather than being built integrally into the body of the heart as in the natural organ. However, the device does, in effect, provide a four chambered pump and thus is structured similarly to the natural heart and has a similar mode of operation.

Figure 3:
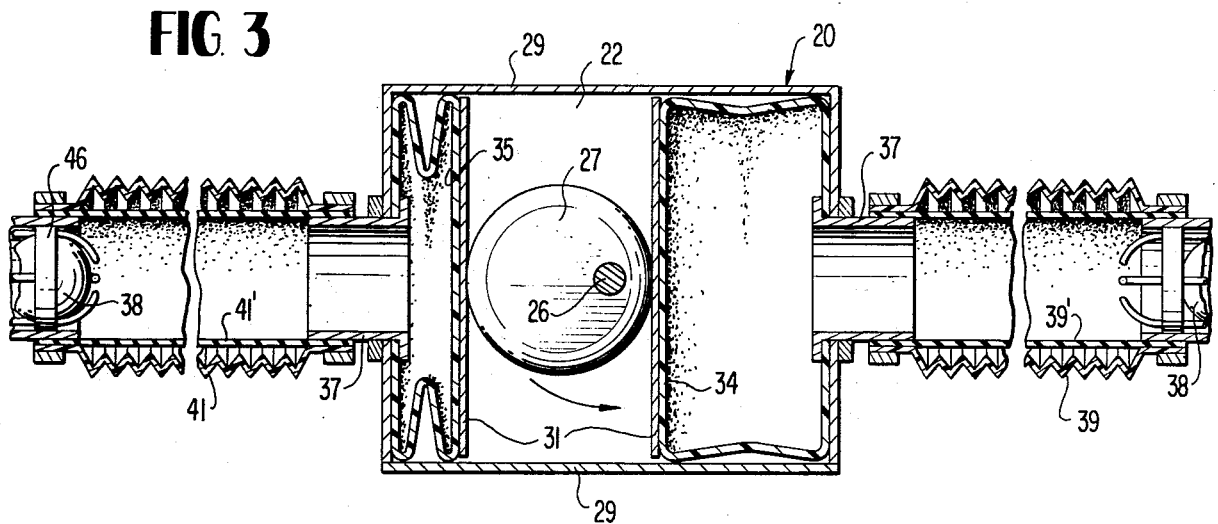
FIG. 3 is a cross sectional view taken on line 3—3 of FIG. 2.
Figure 4:
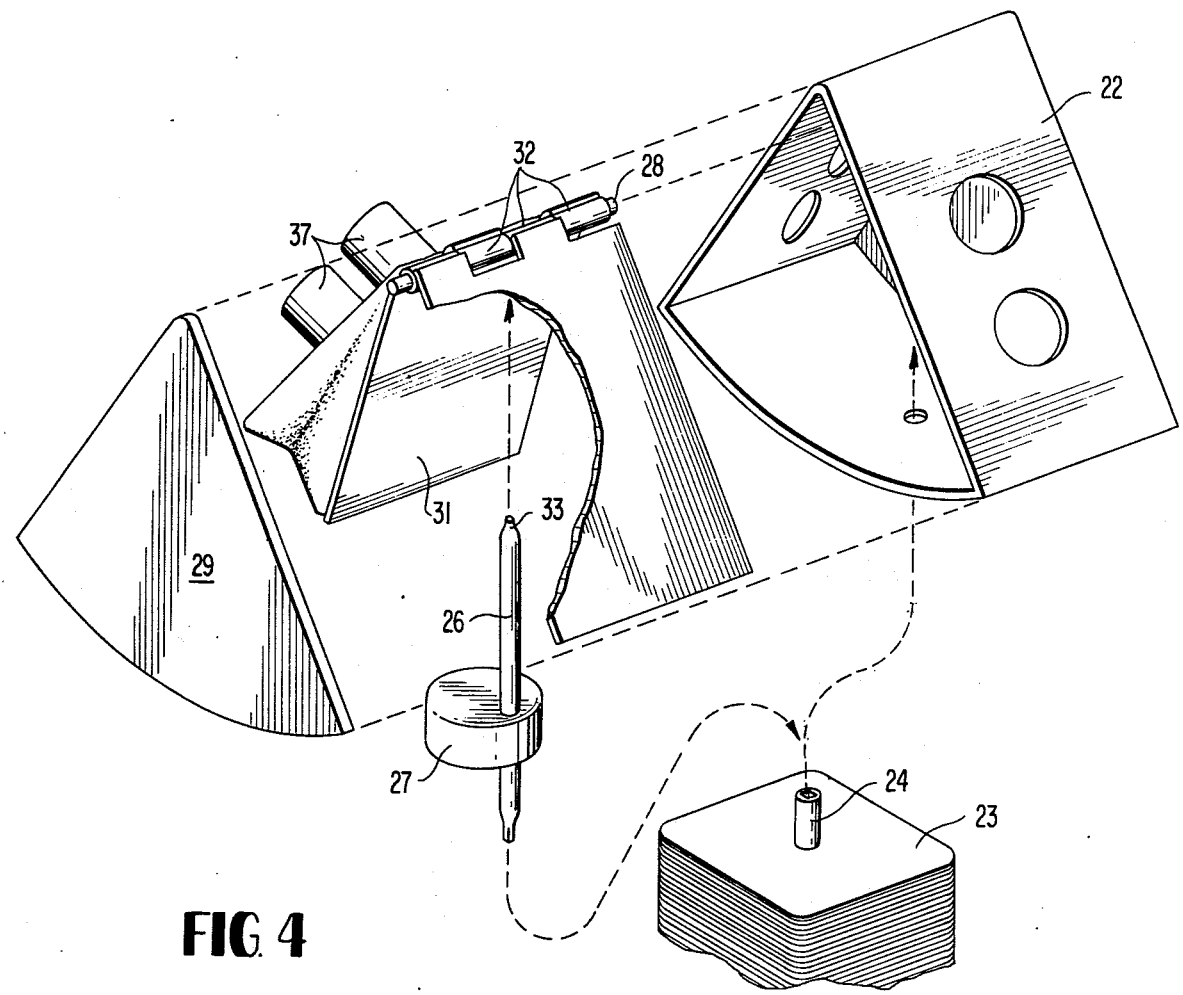
FIG. 4 is an exploded perspective view of the device with parts omitted and parts broken away.

In the same manner, one valve 38 for the right ventricle sac 35 is the blood outflow valve corresponding to one of nature's semilunar valves, and allows blood to pass from the compressed sac 35 to the pulmonary artery 41 while preventing blood flow in the opposite direction. The second valve 38 for the right ventricle sac 35 is the blood inlet or return valve receiving blood from the right atrium 42 and thus corresponds to the tricuspid valve of the natural heart. The four check valves 38 in FIGS. 2 and 3 illustrate the situation when the eccentric cam 27 is turning in the direction of the arrow, FIG. 3, and thus beginning to compress the left ventricle sac 34 while allowing the right ventricle sac 35 to begin its filling and expansion. At this time, the blood outflow valve 38 for the left ventricle sac 34 is open, FIG. 3, while the blood return valve 38 is closed or seated against the seating ring 43 of the caged plastic valve. Similarly and reversely, the blood return or inflow valve 38 for the right ventricle sac 35 is in the open position relative to the seat 44 and the outflow valve 38 for the sac 35 is in closed engagement with the seat 46, FIG. 3.

A further feature of this invention is that the outflow tracts 39 and 41 of the device, aorta and pulmonary outflow, respectively, are double-layered as shown in FIGS. 2 and 3 to provide varying stroke volume depending on filling pressure of the ventricles 34 and 35. The compliant aortic and pulmonic outflow tracts are preferably constructed from an outer accordion-pleated sheath of polyethylene or like tubing, approximately 2.5 cm in diameter. These are lined with latex tubing 39' and 41' approximately 2.2 cm in diameter to allow for some stretching and expansion of the latex tubing in the larger plastic outer sheath. As best shown in FIG. 3, the aortic and pulmonic valves 38 are placed approximately 8 cm beyond or outside of the two ventricular chambers of the device. This valving arrangement and the described compliant double-layered outflow tracts including elastic inner layers 39' and 41' allows the ventricle sac which is filled more tightly to empty more readily, in other words, relates stroke volume to filling pressure.

OPERATION

During operation, as the induction motor 23 turns the shaft 26 and eccentric cam 27 at a predetermined speed, the cam will cause oscillation of the pivoted vanes 31, and the latter will cyclically compress the ventricular sacs 34 and 35. That is to say, one ventricular sac will be compressed to expel blood therefrom while the other sac is allowed to fill with blood and expand. As previously noted, the stroke volume of each ventricular sac is independent of the other sac and is a function of atrial pressure and volume. Thus, ventricular stroke volume in the device will vary as it does in the natural heart.

As the cam 27 and one oscillating vane 31 compresses the left ventricular sac 34, blood will flow through the adjacent outlet valve 38 to the aorta 39, and during compression of the sac 34 blood is prevented from returning to this sac through the second adjacent valve 38 which is closed, FIG. 2. At this time, while the right ventricle sac 35 is filling and expanding as a function of atrial pressure and volume, its associated return flow valve 38 is open and its outflow valve 38 is engaged with the seat 46, FIG. 3, and therefore is closed. When the left ventricle sac 34 is filling and expanding and the right ventricle sac 35 is being compressed, the check valve operation will be reversed to allow the proper passage of blood into and from the respective sacs 34 and 35, as in the natural heart. The described cycle of operation is repetitive and continuous as long as the motor is in operation.

Figure 7:
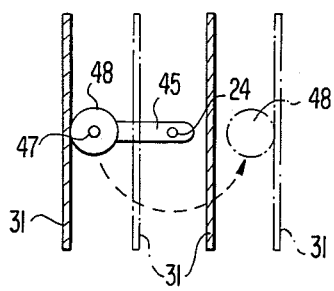
FIG. 7 is a fragmentary horizontal section schematically showing the operation of pumping mechanism.
Figure 5:
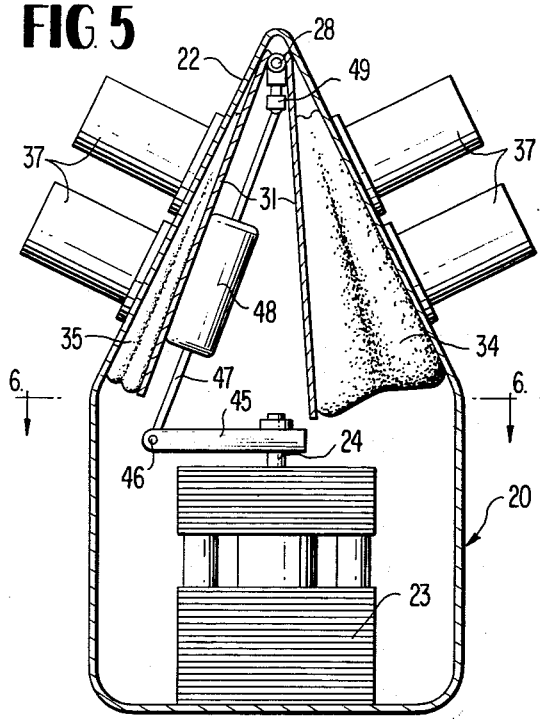
FIG. 5 is a vertical cross sectional view, partly in elevation, through a second embodiment of the invention.
Figure 6:
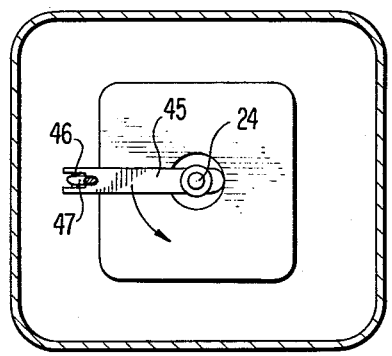
FIG. 6 is a horizontal section taken on line 6—6 of FIG. 5.

In a second embodiment of the invention, FIGS. 5 through 7, the device is essentially unchanged in construction and operation, except that a modified pumping mechanism is employed between the motor shaft 24 and oscillating vanes 31. This modified mechanism includes a radial crank arm 45 secured to and turning with the shaft 24 and pivotally connected at its outer end by an element 46 with a rod member 47 carrying a cylindrical roller 48. The upper end of rod member 47 is connected through a universal joint 49 with the overhead stationary support shaft 28.

As the crank arm 45 turns with the shaft 24, the roller 48 and its supporting rod 47 move in a circular path at the lower end of rod 47, as indicated by the arrow in FIG. 7. However, the universal joint 49 restrains movement of the rod 47 at its top end but allows the rod to swivel freely and universally at such end. Consequently, the roller moves cyclically in a conical path or plane and engages the two vanes 31 cyclically to compress one ventricular sac 34 or 35 while the other sac is allowed to fill and expand in the manner already described. The remaining parts of the device and the overall mode of operation are unchanged from the first embodiment and need not be further described herein.

A third embodiment of the invention is shown in FIGS. 8 through 10 where, again, the device differs from the first embodiment only in the mechanism between the motor shaft 24 and the pumping vane structure, all other parts and their operations remaining unchanged.

Figure 10:
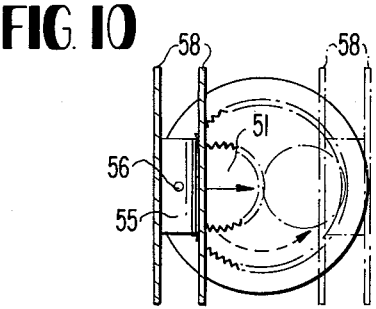
FIG. 10 is a view similar to FIG. 7 illustrating the operation of pumping mechanism.
Figure 8:
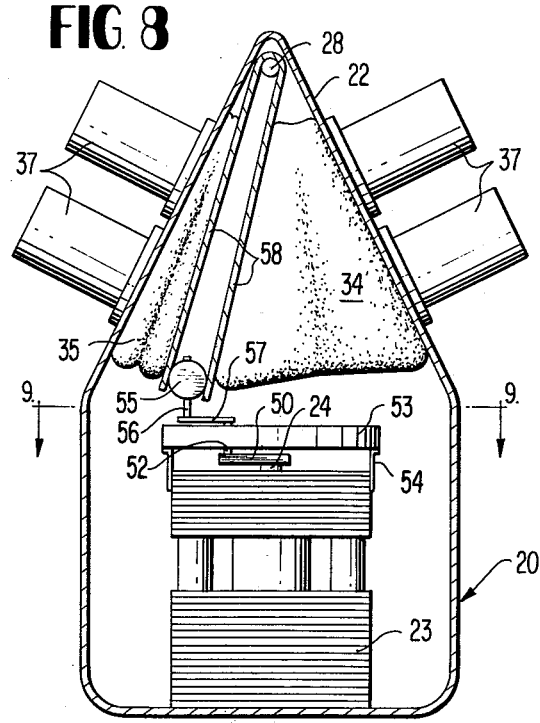
FIG. 8 is a vertical sectional view similar to FIG. 5 showing another embodiment of the invention.
Figure 9:
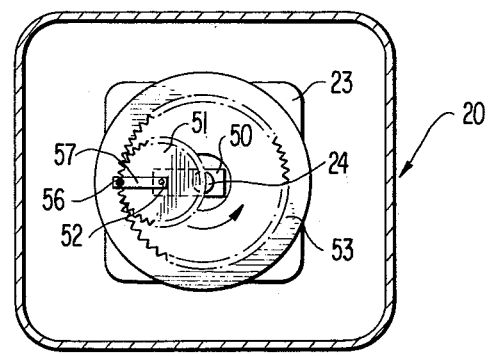
FIG. 9 is a horizontal section taken on line 9—9 of FIG. 8.

In FIGS. 8 through 10, the motor shaft 24 carries a crank arm 50 turning therewith and a first relatively small gear 51 is mounted on the free end of crank arm 50 through a vertical shaft 52 and travels in a circular path with the crank arm as indicated by the arrow in FIG. 10. The smaller gear 51 is in mesh with an internal toothed ring gear 53 having a pitch diameter exactly twice that of the gear 51. The ring gear 53 is fixedly secured to the motor 23 by suitable bracket means 54.

A preferably plastic cylindrical bar or pin 55 is supported above the ring gear 53 on a vertical rod 56 carried by a horizontal arm 57 attached to the shaft 52 of smaller gear 51. The center axis of cylindrical pin 55 is on the axis of rod 56 and this axis is on the pitch circumference of gear 51. With this precise geometric relation, the cylindrical element 55 will traverse or reciprocate back and forth in a linear path across the diameter of the larger stationary gear 53 while the smaller gear 51 rolls around the interior of the ring gear. The linear movement of the element 55 is indicated by the straight arrow in FIG. 10.

A unitary pumping vane having two spaced sides 58 is pivotally mounted on the support shaft 28 and receives the cylindrical element 55 between the vane sides 58 cammingly. Therefore, as the element 55 reciprocates from side-to-side of the pumping chamber 22 in a linear path of movement, the vane sides 58 will cyclically and alternately compress the left and right ventricle sacs 34 and 35.

In all other respects, the mode of operation of the device in FIGS. 8 to 10 is the same as in the prior embodiments.

It is to be understood that the forms of the invention herewith shown and described are to be taken as preferred examples of the same, and that various changes in the shape, size and arrangement of parts may be resorted to, without departing from the spirit of the invention or scope of the subjoined claims.

We claim:

1. A pumping unit adapted for use as a total cardiac replacement device comprising a housing having a wedge-like pumping chamber, a drive motor on the housing externally of the wedge-like pumping chamber and having an output rotary shaft extending through said pumping chamber centrally with the axis of the shaft substantially intersecting the apex of said wedge-like pumping chamber, an eccentric cam element on said shaft within said pumping chamber and turning with said shaft, a support shaft extending within the pumping chamber near and parallel to the apex thereof and substantially perpendicular to the axis of said output rotary shaft, a pair of pumping vanes within the wedge-like pumping chamber on opposite sides of said output rotary shaft and being in contact with said eccentric cam element, corresponding ends of said pumping vanes being independently pivotally connected to said support shaft and supported thereby for independent swinging through the pumping chamber around the axis of the support shaft in response to rotation of the eccentric cam element with said output rotary shaft, a pair of wedge-like pliable compressible sacs in the pumping chamber between said pumping vanes and the converging walls of the wedge-like pumping chamber and being compressed alternately and cyclically by the pumping vanes during rotation of the eccentric cam element, outlet and return conduit means connected in corresponding walls of said pliable compressible sacs and in the converging walls of the pumping chamber, and pairs of oppositely opening and closing check valves connected in said outlet and return conduit means.

2. A pumping unit as defined in claim 1, and said corresponding ends of the pumping vanes carrying hinge knuckles, and said hinge knuckles being rotationally mounted on said support shaft in interfitting relationship.

3. A pumping unit as defined in claim 1, and said wedge-like pumping chamber having parallel tapered end walls abutting the edges of said converging walls, and said pumping vanes comprising substantially rectangular plate vanes which sweep through said wedge-like pumping chamber between the converging walls thereof with opposite edges of the pumping vanes in close proximity to said parallel tapered end walls.

4. A pumping unit as defined in claim 3, and said pumping chamber also including an arcuate wall in spaced relation to said apex and interconnecting said converging walls at their ends away from the apex, the ends of the pumping vanes away from the apex sweeping over the arcuate wall in close proximity thereto.

5. A pumping unit as defined in claim 4, and said wedge-like pliable compressible sacs having pleated end walls away from said apex and adjacent the arcuate wall and folding inwardly and away from the arcuate wall when the sacs are compressed by said pumping vanes.

6. A pumping unit as defined in claim 1, and said outlet and return conduit means including substantially rigid tubular fittings connected to said converging walls of the pumping chamber and serving to secure said corresponding walls of the pliable compressible sacs to the interiors of the converging walls, said tubular fittings additionally serving as housings for said check valves exteriorly of the pumping chamber.

7. A pumping unit as defined in claim 1, and said pliable compressible sacs formed of Dacron reinforced Silastic.

8. A pumping unit as defined in claim 1, and one conduit means on each side of said pumping chamber comprising a double layered outflow tract in which the inner layer of the tract is elastic and of smaller diameter than the outer layer.

* * * * *